United States Patent [19]
Borgford et al.

[11] Patent Number: 5,972,631
[45] Date of Patent: Oct. 26, 1999

[54] SUCROSE DETECTION BY ENZYME-LINKED IMMUNOSORBANT ASSAY

[75] Inventors: Thor Jon Borgford, Burnaby; Kathleen Iris Racher, West Vancouver; Curtis Archie John Braun, Burnaby, all of Canada

[73] Assignee: De Novo Enzyme Corporation, Burnaby, Canada

[21] Appl. No.: 08/962,723

[22] Filed: Nov. 3, 1997

[51] Int. Cl.$^6$ ................................................. G01N 33/533
[52] U.S. Cl. ................ 435/7.9; 435/14; 435/15; 435/18; 435/178; 435/210; 435/7.32; 435/7.1; 435/7.04; 436/518; 436/524
[58] Field of Search ................ 435/14, 15, 18, 435/178, 210, 7.9, 7.32, 7.1, 7.94; 436/518, 524

[56] References Cited

U.S. PATENT DOCUMENTS

| | | | |
|---|---|---|---|
| 4,576,912 | 3/1986 | Yaverbaum et al. | 435/7 |
| 4,687,732 | 8/1987 | Ward et al. | |
| 4,770,994 | 9/1988 | Rittenhouse | 435/7 |
| 4,786,595 | 11/1988 | Arai et al. | |
| 4,970,156 | 11/1990 | Avrameas et al. | |
| 5,045,535 | 9/1991 | Mang | 514/57 |
| 5,177,012 | 1/1993 | Kim et al. | 435/175 |
| 5,605,840 | 2/1997 | Meddings et al. | 436/94 |
| 5,620,899 | 4/1997 | Meddings et al. | 436/63 |

OTHER PUBLICATIONS

Su et al., Carbohydrate Research. 248:339–348, 1993.
Miller et al., Biochim Biophys Acta. 870(2):198–203, 1986.
Mooser et al., Journal of Biological Chemistry. 206(11):6907–6915, 1985.
Wenham et al., J. Gen. Microbiol. 114(part 1):117–124, 1979.
Montville et al., Journal of Dental Research. 56(8):983–989, 1977.
Germaine et al, J. Bacteriol. 120(1):287–294, 1974.

*Primary Examiner*—Christopher L. Chin
*Assistant Examiner*—Bao-Thuy L. Nguyen
*Attorney, Agent, or Firm*—Fitzpatrick, Cella Harper & Scinto

[57] ABSTRACT

A method is described for the rapid, sensitive and accurate determination of sucrose in biological fluids. A substrate is pre-coated with a glucose or fructose polymer and a transglycosidase enzyme. When the coated substrate is incubated with biological fluids containing concentrations of sucrose, the transglycosidase enzyme transfers monomers of glucose or fructose from the sucrose to the glucose or fructose polymer. The dimensions of the polymer are increased in proportion to the sucrose concentration of the samples. Newly formed polymer is subsequently quantitated in an immunoassay which employs either a combination of a carbohydrate-binding protein (which may be an antibody) and a conjugate of a secondary antibody and a marker enzyme, or a conjugate of a carbohydrate-binding protein and a marker enzyme. The assay is accurate at sucrose concentrations below 1 $\mu$g/mL. No interference was observed at glucose concentrations as high as 25 mM. The sucrose detection assay is particularly useful in a non-invasive diagnostic test for gastric damage.

13 Claims, 2 Drawing Sheets

SUCROSE DETECTION BY ENZYME-LINKED IMMUNOSORBANT ASSAY

BACKGROUND OF THE INVENTION

1. Field of the Invention

The invention relates to a method for assaying sucrose in a sample of biological fluid. This method is useful in a non-invasive diagnostic procedure for detection of gastric damage.

2. Related Background Art

It is currently possible to diagnose gastric damage with great accuracy by a medical procedure known as endoscopy (gastroscopy). However, endoscopy is an invasive and undesirable procedure which is, for several reasons, not practical as a general screening method for gastric damage; patients experience considerable discomfort, the procedure is expensive, time consuming and only available in specialized centers. Typically, patients are chosen for endoscopy when they show symptoms of gastric damage or when gastric damage is apparent by radiology. The major shortcoming of current strategies for diagnosis is that many individuals are asymptomatic for gastric damage. They are, therefore, at risk from potentially fatal complications (e.g. gastrointestinal bleeding) if left untreated.

A method for detection of gastric epithelial damage, particularly ulcers and lesions in the stomach, using non-invasive, non-radioactive and non-x-ray techniques or procedures is disclosed in U.S. Pat. No. 5,620,899. This method employs a disaccharide which can be orally administered to a patient. The disaccharide does not transport across cell membranes, is metabolized within the small intestine to its monosaccharide components, and is not broken down elsewhere in the body. Damage to the gastric epithelium will allow the disaccharide to enter the blood without being metabolized. Hence, the disaccharide will appear in the blood or urine to an extent that can be correlated with the extent of gastric epithelial damage. Typically, the disaccharide is administered to a patient, followed by collection of blood or urine, which is assayed for the disaccharide. The use of sucrose in particular as a diagnostic marker in detection of gastric epithelial damage is described in copending U.S. patent application Ser. No. 08/456,203.

A variety of methods are available for the detection and quantitation of sucrose in biological samples including; gas chromatography, high-performance capillary electrophoresis with indirect absorbance detection or laser interference refractive index detection, high-performance anion exchange liquid chromatography with amperometric detection or refractometric detection and mass spectrum analysis. However, sucrose analysis by these methods is unsuitable for high-throughput screening in the clinical laboratory, either because the methods are expensive, require a high degree of technical skill to perform or require specialized equipment.

Direct immunological assays for sucrose have not been devised. Presumably this is because sucrose is a poor antigen or hapten (i.e., poorly antigenic) or perhaps because antibodies raised against sucrose have poor specificity; possibly cross-reacting with glucose and or fructose. Antibodies with specificity for sucrose have not been reported in the literature. However, antibodies with high affinity and high specificity for polymers of glucose and fructose, the carbohydrates which comprise sucrose, are known. For example, antibodies have been characterized that have high specificity for dextran as well as antibodies with high specificity for levan. Though there are no reports of antibodies directed to glycogen (glycogen is a storage polysaccharide common to all vertebrates and hence unlikely to be antigenic), some well characterized proteins exist which bind specifically to the amylose portion of the glycogen polymer. Most notable of these is the amylose-, or maltose-binding protein of *Escherichia coli*.

An immunological assay for sucrose, suitable for use in clinical laboratories, would be extremely useful in conjunction with a non-invasive diagnostic procedure for detecting gastric damage.

SUMMARY OF THE INVENTION

This invention is directed to a method for assaying sucrose in a biological fluid. The method comprises the steps of: (a) coating a substrate with (i) a glucose or fructose polymer selected from the group consisting of amylose, dextran and levan and (ii) a sucrose transglycosidase enzyme corresponding to the selected glucose or fructose polymer; (b) incubating the coated substrate with a biological fluid; and (c) determining an amount of sucrose present in the fluid by measuring an increase in an amount of the glucose or fructose polymer.

In two preferred embodiments of this invention, step (c) may be carried out in two ways. The first comprises the steps of: (a) incubating the substrate with a carbohydrate-binding protein, which may be an anti-dextran antibody if the substrate is coated with dextran, an amylose-binding protein if the substrate is coated with amylose, or an anti-levan antibody if the substrate is coated with levan; (b) incubating the substrate with a secondary antibody; and (c) adding a solution containing a detecting agent, and determining the amount of sucrose in the fluid by measuring light absorption of the solution.

In the second preferred embodiment, step (c) is carried out by: (a) incubating the substrate with a conjugate comprising (i) a carbohydrate-binding protein, which may be an anti-dextran antibody if the substrate is coated with dextran, an amylose-binding protein if the substrate is coated with amylose, or an anti-levan antibody if the substrate is coated with levan; and (ii) a marker enzyme; and (b) adding a solution containing a detecting agent, and determining the amount of sucrose in the fluid by measuring light absorption of the solution.

DETAILED DESCRIPTION OF THE INVENTION

Figure 1:
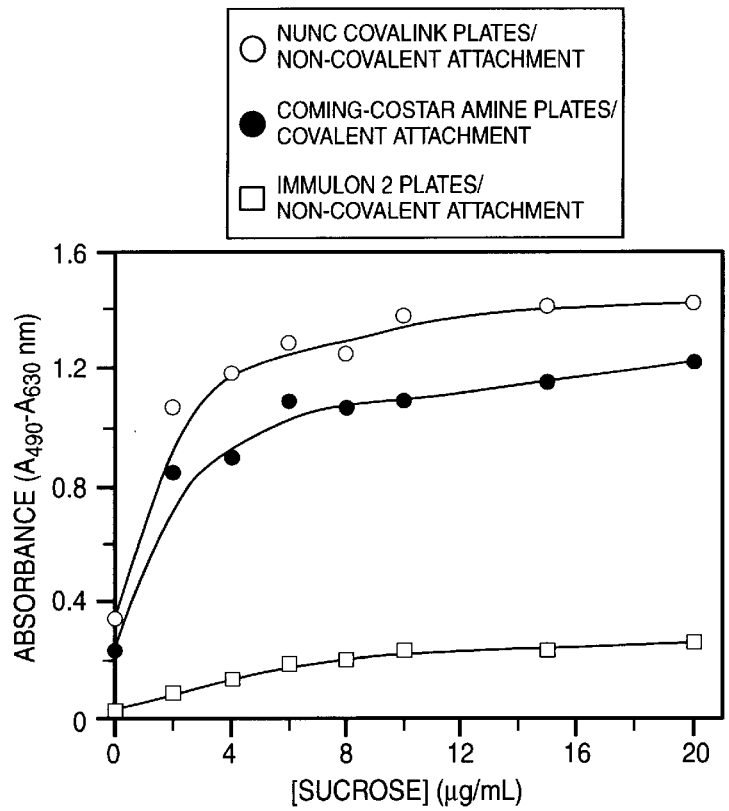
FIG. 1 is a graph showing the measured absorbance as a function of sucrose concentration for three different commercial immunological test plates.

In this invention, sucrose is detected and measured by an indirect immunological method in which free sucrose is first converted to an antigenic polymer. Any of the three known transglycosidase enzymes, which accomplish the conversion of sucrose to a polymer comprised of one of its hexose constituents, glucose or fructose, may be used in this method. These enzymes are amylosucrase, dextransucrase, and levansucrase. The enzyme amylosucrase synthesizes a glycogen-like polymer (α, 1–4 glycosidic linkages) from the glucose component of sucrose and releases fructose. Similarly, the enzyme dextransucrase synthesizes dextran (β, 1–6 glycosidic linkages) a polymer of glucose from sucrose and releases fructose. Levan sucrase differs from the former two enzymes in that it synthesizes levan (2–6, α-D fructan) a polymer of fructose while glucose is released. The preferred transglycosidase enzyme in the method of this invention is dextransucrase.

Although it is possible for the transglycosidase enzymes to synthesize polymers starting only with sucrose, the usual practice is to use a primer to initiate the polymerization. The primer may be as small as a disaccharide or trisaccharide, or it may be a glucose or fructose polymer, in which case the enzyme will extend the polymer to one of higher molecular weight. In a preferred embodiment of this invention, where dextransucrase is the transglycosidase enzyme, dextran is the preferred primer. Preferably, dextran having a molecular weight in the range from about 11.5 kDa to about 71 kDa, and most preferably dextran having a molecular weight of about 41 kDa (obtained from Sigma Chemical Company, St. Louis, Mo.), is used as a primer.

The first step of the method of this invention is to attach the primer to a support surface, referred to hereinafter as a substrate. Typically, the substrate is a plate containing wells designed to hold suitable volumes of reagents for the assay method. Attachment of the primer to the substrate prevents the primer from being dislodged during washing operations carried out during the method. The means of attachment may be either covalent or non-covalent.

Examples of covalent means include reductive amination to bond the primer to an amine-functionalized plate, or any other chemical method that leads to the activation of the hydroxyl groups on the dextran polymer so that they will react with a nucleophilic group on the plate. Reductive amination is typically accomplished by adding a reducing agent to the primer solution. Suitable reducing agents include, for example, sodium cyanoborohydride, sodium borohydride, hydrogen in the presence of a hydrogenation catalyst, zinc and hydrochloric acid, and formic acid. Covalent attachment of the primer is generally disadvantageous due to the much higher cost of functionalized substrates and the additional manipulation associated with the preparation of covalently derivatized plates.

A primer is attached by non-covalent means by allowing it to passively adsorb onto the surface of the substrate from a buffered solution of the primer. The preferred pH range for the buffered primer solution is from about 7.0 to about 8.0, most preferably from about 7.4 to about 7.5. The preferred buffer solution is phosphate-buffered saline solution.

After attachment of the primer to the substrate, the unbound primer is preferably removed by washing the substrate. Typically, this is accomplished by means of multiple washings with distilled deionized water, or with a suitable buffer at a pH near neutrality, e.g., 1 X phosphate buffer solution. The substrate is then blocked by incubation with a phosphate buffer solution containing a surfactant, for example Tween 20 (Sigma Chemical Co.), and ovalbumin, and then washed with distilled deionized water.

The coated substrate is next treated with a solution of the transglycosidase enzyme. This solution may also contain a surfactant. Suitable surfactants include, for example, Triton X-100 (Sigma Chemical Co.). Surfactants are typically present from about 0.1% to about 1.5% by weight of the solution, preferably from about 0.5% to about 1.0% by weight of the solution. Most preferably, the transglycosidase enzyme is added in a 250 mM sodium phosphate buffer of pH 6.0, containing 1% Triton X-100. The substrate and solution are generally incubated at about room temperature for a period of about 30 minutes to about 120 minutes, preferably from about 30 minutes to about 45 minutes. Preferably, excess transglycosidase enzyme is removed by washing the substrate. Typically, this is accomplished by means of multiple washings with distilled deionized water, or with a suitable buffer at a pH near neutrality.

A biological fluid, buffered to a pH in the range from about 6.3 to about 6.7 with a phosphate buffer, is then allowed to react with the substrate. Preferably, an approximately equal volume of 0.5 M sodium phosphate buffer solution is added to the biological fluid. Generally, the substrate and the fluid are incubated at a temperature in the range from about 21° C. to about 42° C., preferably from about 30° C. to about 37° C., and most preferably about 30° C., for a period of about 30 minutes to about 120 minutes, preferably from about 30 minutes to about 45 minutes. Preferably, excess biological fluid is removed by washing the substrate. Typically, this is accomplished by means of multiple washings with distilled deionized water, or with a suitable buffer at a pH near neutrality.

In a first preferred embodiment of this invention, the substrate is then treated with a carbohydrate binding protein which will bind to dextran, if the transglycosidase enzyme used in the method produces a dextran polymer, amylose if the transglycosidase enzyme used in the method produces an amylose polymer, or levan, if the enzyme produces a fructose polymer. An example of such carbohydrate binding proteins, which may be antibodies, is mouse anti-dextran antibody. In a preferred embodiment of the invention, wherein the glucose or fructose polymer is dextran and the transglycosidase enzyme is dextransucrase, the preferred antibody is mouse anti-dextran antibody. The antibody is typically added to the substrate in an aqueous solution, which may also contain buffers and surfactants. The preferred pH range for the buffered primer solution is from about 7.0 to about 8.0, most preferably from about 7.3 to about 7.5. Preferred buffer solutions include phosphate-buffered saline solution, or any other buffer solution with the appropriate pH range. The most preferred buffer solution is phosphate-buffered saline solution. The solution may also contain a surfactant. Suitable surfactants include, for example, Tween 20 and Triton X-100. Surfactants are typically present from about 0.1% to about 1% by weight of the solution, preferably from about 0.4% to about 0.6% by weight of the solution. The substrate and the antibody are incubated at a temperature in the range from about 21° C. to about 42° C., preferably from about 35° C. to about 39° C., and most preferably about 37° C., for a period of about 15 minutes to about 120 minutes, preferably from about 30 minutes to about 45 minutes. Preferably, excess antibody is removed by washing the substrate. Typically, this is accomplished by means of multiple washings with distilled deionized water, or with a suitable buffer at a pH near neutrality.

In the first preferred embodiment of this invention, the substrate is next treated with a secondary antibody. Preferably, the secondary antibody is a conjugate comprising an antibody which will bind to the primary antibody or carbohydrate binding protein and a marker enzyme. The marker enzyme may be any enzyme which catalyzes a reaction in a detecting agent producing a detectable light absorption. Examples of suitable marker enzymes include peroxidase enzymes and alkaline phosphatase enzymes. The preferred marker enzymes are the peroxidase enzymes. In a preferred embodiment of the invention, wherein the glucose or fructose polymer is dextran, the transglycosidase enzyme is dextransucrase, and the preferred antibody is mouse anti-dextran antibody, the conjugate preferably comprises goat anti-mouse IgG and horseradish peroxidase. The substrate and the conjugate are incubated at a temperature in the range from about 21° C. to about 42° C., preferably from about 35° C. to about 39° C., and most preferably about 37° C., for a period of about 15 minutes to about 120 minutes, preferably from about 30 minutes to about 45 minutes. Preferably, excess antibody is removed by washing the substrate. Typically, this is accomplished by means of multiple washings with distilled deionized water, or with a suitable buffer at a pH near neutrality.

In a second preferred embodiment of this invention, the addition of a secondary antibody may be eliminated by addition of a conjugate of the carbohydrate binding protein and a marker enzyme to the coated substrate. The conjugate binds to the glucose or fructose polymer and also provides the necessary marker enzyme. The marker enzyme may be any enzyme which will catalyze a reaction in a detecting agent to produce a detectable light absorption. Such conjugates may be prepared by known methods, including for example, the methods described in M. Imigawa et al., Journal of Applied Biochemistry, Vol. 4, page 41 (1982); and E. Ishikawa et al., Journal of Immunoassay, Vol. 4, page 209 (1983), and embodied in kits produced by Pierce Corp., Rockford, Ill., under the names EZ-Link™ Plus Activated Peroxidase Kit, EZ-Link™ Peroxidase Kit, EZ-Link™ Maleimide Activated Horseradish Peroxidase Kit, and EZ-Link™ Maleimide Activated Alkaline Phosphatase Kit. The most preferred method is embodied in the EZ-Link™ Plus Activated Peroxidase Kit. Antibody protein is coupled to horseradish peroxidase via periodate oxidation of sugar residues in the peroxidase, followed by reaction of the primary amines of the antibody with the oxidized sugar residues, followed by reductive amination using sodium cyanoborohydride.

Finally, the substrate is treated with a solution containing a detecting agent. The detecting agent, in combination with the marker enzyme, produces a solution having a detectable light absorption. Examples of suitable detecting agents for use when the marker enzyme is peroxidase include a combination of a compound which oxidizes to form a chromophore which strongly absorbs visible light, and an oxidizing agent. Preferably, the detecting agent comprises hydrogen peroxide and either o-phenylenediamine or 3,3', 5,5'-tetramethylbenzidine (TMB). Most preferably, the detecting agent comprises hydrogen peroxide and o-phenylenediamine. The detecting agent is allowed to react at about room temperature in the dark for about 15 minutes to about 30 minutes. The solution may also contain a buffer. The preferred pH range for the buffered solution is from about 5.8 to about 6.2, most preferably from about 5.9 to about 6.1. Preferred buffer solutions include sodium acetate buffer solution. The most preferred buffer solution is 0.1 M sodium acetate. Preferably, an acid is added to the solution at the end of the reaction period to prevent further development of color. Preferred acids are sulfuric acid, hydrochloric acid or orthophosphoric acid. The most preferred acid for this purpose is sulfuric acid. Suitable detecting agents when the marker enzyme is alkaline phosphatase include compounds which form chromophores upon hydrolysis of a phosphate substituent.

The absorbance of the solution after treatment with the detecting agent may be measured using an instrument adapted for measuring absorbance of small amounts of solution on a substrate. An exemplary instrument that is preferably employed in the method of this invention is a microplate reader.

Absorbance of the solution is measured in the visible range at a suitable wavelength for detecting the chromophore present in the solution. In a preferred embodiment of the invention, wherein o-phenylenediamine is oxidized to produce a chromophore, absorbance measurements are made at about 490 nm and at about 630 nm. The difference between the absorbance at 490 nm and the absorbance at 630 nm is proportional to the amount of sucrose present in the biological fluid. If plates of good quality are used, it is also possible to obtain good results using only the absorbance measurement at 490 nm.

The examples which follow are intended as illustrations of certain preferred embodiments of the invention, and no limitation of the invention is implied.

EXAMPLE 1

Preparation of Derivatized 96-Well Polystyrene Plates

A stock solution of dextran, nominally 41 kDa (Sigma Chemical Co., St. Louis, Mo.), was prepared by dissolving 25 mg of the polysaccharide in 10 mL of phosphate buffered saline (PBS) (8.0 $g.L^{-1}$ NaCl, 0.2 $g.L^{-1}$ KCl, 2.17 $g.L^{-1}$ $Na_2HPO_4$, 0.2 $g.L^{-1}$ $KH_2PO_4$). Serial dilutions were made in PBS for a final concentration of $2.5 \times 10^{-6}$ g dextran per 100 mL. Aliquots of the diluted solution were applied to Immnulon 2 plates (Dynatech Inc., Chantilly, Va.) with a multichannel pipettor to a final volume of 100 µL per well. Plates were covered with Parafilm (Fisher Chemical Co., Chicago, Ill.) and incubated at 37° C. for a period of 4 hours. Unbound dextran was removed by washing each well with $3 \times 250$ µL of distilled and deionized water ($ddH_2O$) using an automated Model 1250 Immunowash plate washer (BioRad, Hercules, Calif.). Derivatized plates were air-dried and stored under vacuum in laboratory desiccators until needed.

EXAMPLE 2

Preparation of Streptococcus sanguis Dextransucrase (a) Fermentation of *S. sanguis*.

*Streptococcus sanguis* was obtained from the American Type Culture Collection (ATCC number 10558) and liquid nitrogen storage stocks were prepared as described in Gherna, R. L., Manual of Methods for General Microbiology, Chapter 12 (1981), which is incorporated herein by reference. Freezer stocks of *S. sanguis* were revived by streaking aliquots of frozen culture on brain-heart infusion (BHI) agar plates (37 $g.L^{-1}$ Difco BHI, 15 $g.L^{-1}$ Difco agar) (available from Difco, Detroit, Mich.). Cultures were grown anaerobically at 37° C. overnight in BBL Gaspak Anaerobic Growth Jars (BBL, Cockeysville, Md.) containing Gaspak $CO_2$ envelopes. Growth Jars were prepared according to the manufacturer's instructions. Single colonies were picked from plates and used to inoculate 2×4.0 mL tubes of BHI broth (37 $g.L^{-1}$ Difco BHI) containing 1% glucose. Broth cultures were grown anaerobically overnight in Gaspak Anaerobic Growth Jars, without shaking, until cultures appeared turbid. Cells were expanded by transferring both 4 mL broth cultures to 475 mL of BHI broth containing 1% glucose. Cultures were incubated at 37° C. anaerobically, without shaking, overnight and used as inocula for fermenter cultures.

Large-scale fermentation was performed in a Chemap 20 L fermenter with a working volume of 15 liters. BHI broth was prepared by dissolving 555 g of BHI powder in 8 L of distilled water ($dH_2O$) with heating. The concentrated media was pre-filtered using a Pellicon tangential flow filtration system (Millipore, Bedford, Mass.) equipped with a 10,000 molecular cutoff (MWCO) filter according to the manufacturer's instructions. Consequently, macromolecules exceeding 10,000 kDa were removed from the broth. Prefiltered broth was transferred to the 20 L fermenter culture vessel and diluted to 15 L with $dH_2O$. The broth was subsequently autoclaved at 121° C. for 20 minutes in situ. *S. sanguis* culture from above (475mL) was transferred to the fermenter along with 800 mL of sterile 20% glucose (for a final concentration of 1% glucose). The fermentation was carried out at 37° C., with stirring at 80 rpm but no aeration. The pH and optical density (600 nm) of the culture were measured hourly. Accordingly, the pH was adjusted hourly beginning with the fourth hour of culture to 7.0 by the addition of sterile 1 M NaOH. When the culture reached the stationary growth phase as determined by the lack of change in the $O.D._{600}$ reading within a one-hour time period (after approximately 13 hours) the broth was cooled to 12° C. and transferred to a clean 20 L carboy for further processing.

(b) Concentration of Dextransucrase from *S. sanguis* Culture Supernatant.

A Pellicon tangential flow filtration system (Millipore) assembled with a 0.45 μm membrane and operated according to the manufacturer's instructions was used to separate cells from the culture broth described in part (a). After filtration, phenylmethylsulfonylfluoride (PMSF) was added to the culture supernatant from a 100 mM stock solution in isopropanol to a final concentration of 0.1 mM. The supernatant was then concentrated using the Pellicon tangential flow filtration system equipped with a 100,000 MWCO filter. After concentration to a final volume of approximately 1 L, $dH_2O$ was added to the concentrated filtrate in one-liter aliquots and the ultrafiltration repeated until the conductivity of the filtrate was reduced to 100 $\mu S.cm^{-1}$. A second aliquot of PMSF (0.1 mM) was added to the filtrate.

(c) Purification of Dextransucrase by Affinity Chromatography.

Affinity chromatography of Dextransucrase was performed as described in Mayer, R. M., Methods Enzymol., Vol. 138, p. 649 (1987), which is incorporated herein by reference. A chromatography column, 2.5 cm diameter and 22 cm long, packed with Sephadex G-200 (Pharmacia) and equilibrated in 10 mM sodium phosphate, pH 6.4, was loaded with 500 mL of the filtrate prepared as described in part (b). The column was then washed with approximately 400 mL of degassed running buffer (10 mM sodium phosphate, pH 6.4) at a flow rate of 0.5 $mL.min^{-1}$ until the baseline absorbance of the column effluent at 280 nm returned to zero. Bound dextransucrase was subsequently eluted with elution buffer (10 mM sodium phosphate, pH 6.4 with 0.1% sodium dodecyl sulfate). Five-milliliter fractions were collected and assayed for the presence of dextransucrase using the procedure described in Example 4. Dextransucrase typically eluted in fractions 15 through 20. Fractions containing dextransucrase were pooled and dialyzed against $ddH_2O$ using TM 3–15 mL Slide-a-Lyzer cassettes (Pierce, Rockford, Ill.). Dextransucrase prepared in this manner was flash frozen and stored in 500 μL aliquots at −20° C.

The purification described in this part has been found not to be strictly necessary. The concentrated enzyme may be used in the next step without compromising the enzyme activity. This avoids the yield loss incurred in the purification.

EXAMPLE 3

Preparation of Monoclonal Antibodies to Dextran (a) Revitalization of Mouse NS1 Cell Line for use in Fusions.

Monoclonal antibodies were prepared by an adaptation of methods described in Harlow, et al., Antibodies—A Laboratory Manual, Cold Spring Harbor Laboratory, (1988), which is incorporated by reference herein. Each of two BalbC mice were injected intraperitoneally with 500 μL of pristaine (2,6,10,14-tetramethylpentadecane). Concurrently, an existing 20 mL mouse NS1 cell culture was grown in 20% Fetal Calf Serum (FCS, Gibco, Gaithersburg, Md.); Dulbecco's Modified Eagle Medium (DMEM, Gibco) at 37° C. and 10% $CO_2$ in Corning 80 $cm^2$ tissue culture flasks using a Forma Scientific Water-Jacketed Incubator. This culture was split 10:1 producing 4 new 20 mL 20% FCS:DMEM cultures. After four days of growth when the cultures had reached approximately 2 million cells per flask they were centrifuged at 1000 rpm at room temperature in 15 mL Falcon polystyrene tubes then resuspended in a total of 1 mL of DMEM. Five hundred microliters of this suspension was injected intraperitoneally into each mouse previously injected with pristaine. After one week, a large tumor was evident in the abdomen of the mice. One mouse was sacrificed using $CO_2$ gas and the abdominal fluid removed aseptically with a syringe. The fluid was divided equally between two 15 mL Falcon tubes and 10% FCS:DMEM was added to a final volume of 13 mL. A 0.5 mL aliquot was removed from each tube and used to inoculate a tissue culture flask containing 20 mL of 10% FCS:DMEM. The cell line was maintained in flask culture by continued subculturing into fresh media.

(b) Liquid Nitrogen Storage and Thawing of Cell Lines.

After the removal of aliquots according to Section 3.1 the remaining 2×12.5 mL of NS1 culture was centrifuged at 1000 rpm for 2 minutes and the media was carefully removed. To each tube 10 mL of 70% DMEM, 20% FCS, and 10% dimethylsulfoxide (DMSO) was added and the cells were gently resuspended. One milliliter aliquots of resuspended cells were transferred to 2.0 mL Corning Disposable Sterile Cryogenic Vials. The vials were placed at −70° C. overnight and then into liquid nitrogen the following day. Cultures were stored in liquid nitrogen until needed. Frozen stocks were thawed by placing cryovials in a 37° C. water bath. The thawed contents were then added to a culture flask containing 20 mL of 10% FCS/DMEM and incubated overnight at 37° C. under 10% $CO_2$. The cells were precipitated by centrifugation at 1000 rpm and resuspended in 20 mL of fresh media. This procedure reduced the DMSO present during storage.

(c) Immunization of Mice and Titering of Immunological Response.

A 2.5 $mg.mL^{-1}$ solution of dextran (5–40 MDa molecular weight, ICN Biomedicals, Aurora, OH) in PBS was combined with an equal volume of Freund's incomplete adjuvant (Gibco) and vortexed to homogeneity. Each of several BalbC mice were injected subcutaneously with 100 μL of the above mixture (250 μg dextran per mouse). After one week the tips of the tails of the mice were clipped and a glass capillary tube was used to collect approximately 20 μL of blood. A 200 μL aliquot of PBS was added to the blood and the mixture was centrifuged for 5 minutes at 13000 rpm using a Baxter Canlab Biofuge 13 (Baxter, Toronto, Ontario) to remove cells and particulates. The clarified samples were stored at 4° C. until needed. Immulon 2 plates were coated, as described in Example 1, by incubation for 2 hours at 37° C. with 200 μL per well of a 0.25% solution of dextran (5–40 MDa molecular weight) in PBS. After washing with distilled water the plates were blocked by incubating them overnight at 4° C. with 100 μL per well of blocking buffer (PBS; 0.5% Tween-20 (Sigma Chemical Co., St. Louis, Mo.); 0.5% ovalbumin (Sigma)). Each clarified blood sample was diluted 100, 1000, and 10000 fold in PBS and applied at 100 μL per well to the derivatized polystyrene plates. After a one hour incubation at 37° C., the plates were washed three times with ddH$_2$O and a secondary antibody added. Goat anti-mouse peroxidase (GAM peroxidase, Gibco), 100 μL diluted 1000×, was added to each well in blocking buffer. The secondary antibody was incubated with each well at 37° C. for one hour and the plates subsequently washed three times with ddH$_2$O. To develop the plates 100 μL per well of substrate was added (35 mL 0.1 M sodium acetate, pH 6.0; 35 mg o-phenylenediamine (OPD); 35 μL hydrogen peroxide). The plates were left at room temperature for 5 minutes after which 25 μL of 20% sulfuric acid was added to each well to terminate the reaction. The absorbance of each well was recorded at 630 nm and 490 nm on a Molecular Devices SpectraMAX 340 microplate reader. The absorbance was corrected by subtracting the measurement at 630 nm from that at 490 nm. The above procedure (i.e., beginning with the injection of dextran) was repeated two more times allowing two weeks between injections.

(d) Fusion of Immunized Spleen Cells with Myeloma NS1 Cells.

The mouse exhibiting the strongest immunological response, as determined by the immunization/titering procedure described in part (c), was chosen for fusion experiments. The mouse was injected intraperitoneally with 250 μg of dextran (5–40 MDa molecular weight) in 100 μL PBS with no adjuvant. Fusion was performed 5 days after the injection. On the day prior to dextran injection a 1:1 split of revitalized NS1 cells was performed giving two 20 mL culture flasks of cells for fusion (see part (a)). On the day of the fusion, 100 mL of HAT media was prepared (20 mL FCS, 1.0 mL 100× HAT Supplement (Gibco), 79 mL DMEM, Interleukin-6 (IL-6) (Boehringer-Mannheim) to 1.0 ng/mL). The following two procedures were timed to end simultaneously:

(i) NS1 cell preparation: The contents of the two 20 mL flasks of cells, prepared as described above, were pooled and then evenly distributed into 4×15 mL Falcon tubes. Tubes were centrifuged at 1000 rpm for 5 minutes in a Baxter Canlab Biofuge 13. Media was removed by aspiration, the cells resuspended in 5 mL DMEM per tube and tubes were centrifuged again. After removal of the supernatant, the cells were resuspended with 2.5 mL DMEM per tube, pooled into one tube, and recentrifuged. The final pellet was resuspended with 7 mL of DMEM.

(ii) Spleen cell preparation: The most appropriate mouse, as judged by antibody titers, was sacrificed using CO$_2$ gas. The spleen was removed aseptically and transferred to a Petri dish containing 10 mL of DMEM. The spleen was disrupted by compression against the plate bottom with cheesecloth and the head of a plastic syringe plunger. The fluid containing the individual cells freed by this process was transferred to a 15 mL Falcon tube and centrifuged at 1000 rpm for 5 minutes. After the media was removed, 7 mL of DMEM was added to resuspend the cells.

The final 7 mL suspensions of parts (i) and (ii) were pooled into one tube and spun at 1000 rpm for 5 minutes. After removing the supernatant, 2 mL of 500 polyethylene glycol 4000 (Gibco) was added slowly over a 2 minute time period during which the mixture of cells was stirred with the tip of the pipette. Subsequently, 10 mL of DMEM was added slowly over a seven-minute period with the first 2 mL being added very slowly. The mixture was then centrifuged at 1000 rpm for 5 minutes, the media removed and the pellet resuspended with 10 mL of HAT media. Once resuspended the 10 mL was then combined with the remaining 90 mL of HAT media. This solution was then transferred to 5 Corning Cell Wells plates (200 μL per well).

(e) Screening of Hybridomas.

Approximately 7 to 10 days after fusion, hybridomas were visualized. Five Immulon 2 plates were prepared as described in Example 3(c) for titering mice. Media, 70 μL, was removed from each of the wells of the hybridoma plates and transferred to the wells of the Immulon 2 plates. The procedure for the mouse titering was repeated as described in Example 3(c) except that a 30 minute peroxidase development period was used.

(f) Serial Dilutions of Responsive Hybridomas.

Wells containing hybridomas giving a positive signal during the screening process were selected for serial dilution to obtain clonal populations of cells. For each positive well a corresponding Corning plate was filled with 100 μL per well of HT media (HAT media containing HT Supplement (Gibco) instead of HAT Supplement). The contents of the positive well were agitated with a pipette tip and 100 μL of suspended cells were added to the top-left corner well of the Corning plate. The contents of the well were then diluted 1:1 serially downwards into the eight wells of the plate beneath. The eight wells containing serially diluted antibody, were then topped to 200 μL with HT media and diluted 1:1 horizontally across the plate. All wells on the plate were eventually topped to 200 μL with HT. Seven to 10 days later when hybridomas appeared the screening process was repeated as well as serial dilutions of positive clones. After a third round of screening and serial dilution, isolated hybridomas were grown on 10% FCS:DMDM:IL-6.

(g) Large Scale Expansion and Freezing of Clones.

Stable monoclonal lines were expanded by increasing the culture volumes from 200 to 500, 1000 and finally 2500 μL. At each stage 100 μL of suspended cells were added to 900 μL of 70% DMEM, 20% FCS, 10% DMSO for storage in liquid nitrogen (described in Example 2) as backup stocks.

(h) Preparation of Ascites Fluid.

Large quantities of antibody were produced in ascites fluid. This was accomplished in much the same way that the NS 1 cells were revitalized in Example 3(a). Two mice were injected intraperitoneally with pristaine. Meanwhile 4×20 mL 10% FCS/DMEM/IL-6 hybridoma cultures were prepared. When the cultures had reached approximately 2 million cells per flask they were centrifuged at 1000 rpm at room temperature in 15 mL Falcon tubes. The cells were resuspended in a total of 1 mL DMEM and 500 μL was injected intraperitoneally into each mouse. One week later, after abdominal tumors had developed, the mice were sacrificed using CO$_2$ and the abdominal fluid was removed aseptically with a syringe to 15 mL Falcon tubes. These tubes were spun at 1000 rpm and the antibody-rich supernatant collected.

EXAMPLE 4

Sucrose Detection by Enzyme-Linked Immunosorbant Assay

A fresh aliquot of dextransucrase, prepared as described in Example 2, was thawed and diluted ten-fold in 1% (v/v) Triton X-100. The enzyme solution was then added to a dextran derivatized plate, prepared as described in Example 1, at 50 μL/well. The enzyme solution was incubated with the derivatized plate for 30 minutes at room temperature. Unbound enzyme was subsequently washed from the plate with 250 μL per well of ddH$_2$O.

Sucrose standards, ranging in concentration from 0 to 10 μg.mL$^{-1}$ (in 50 mM sodium phosphate, pH 6.0; 0.50%. Triton X-100) were added to enzyme and primer coated plates (8 replicates on each plate) and were incubated for 15 minutes at 30° C. The plate was then washed three times with 250 μL of ddH$_2$O. Mouse anti-dextran antibody, prepared as described in Example 3, was diluted 10,000-fold in antibody buffer (PBS containing 0.5% Tween-20 and 0.5% ovalbumin) and was added to the plate at 100 μL/well and incubated for 30 minutes at 37° C. The unbound primary antibody was removed by washing with ddH$_2$O (as described above for dextransucrase). The secondary antibody (goat anti-mouse peroxidase conjugate, Gibco) was diluted 1000-fold in antibody buffer, added to the plate at 100 μL per well and incubated for 30 minutes at 37° C. Unbound secondary antibody was removed by washing with ddH$_2$0 as described previously. Freshly prepared substrate (100 μL of 2 mg.mL$^{-1}$ o-phenylenediamine and 1 AL.mL$^{-1}$ hydrogen peroxide in 0.1 M sodium acetate, pH 6.0) was added to each well and after 30 minutes at room temperature the reaction was stopped by the addition of 25 μL per well of 20% H$_2$SO$_4$. The absorbance (490–630 nm) readings were obtained using a Molecular Devices SpectraMAX 340 microplate reader.

EXAMPLE 5
Comparison of Commercial ELISA Plates

Different commercial ELISA plates with covalently, and non-covalently attached 41 kDa dextran primer, were evaluated for the method of this invention. The plates used were: NUNC Covalink plates (VWR Canlab, Toronto, Ontario) and non-covalently attached dextran (open circles); Corning-Costar amine plate with covalently attached dextran (closed circles); and Immulon 2 plates with non-covalently attached dextran (open squares). Plate derivatization conditions were as follows: (a) non-covalent derivatization; NUNC Covalink—100 μL per well of a 0.25% dextran solution in 5% Triton X-100; Immulon 2 (VWR Scientific or Dynatech Inc.)-100 μL per well of a 2.5×10$^{-9}$% dextran solution in PBS; plates were incubated with the dextran solutions at 37° C. for 4 hours; (b) covalent derivatization; Corning Costar plates (Fisher Scientific)-300 μL per well of a solution containing 3.75% sodium cyanoborohydride, 0.25% dextran in 5% Triton X-100, plates were incubated overnight at 52° C. After derivatization, plates, covalent and non-covalent, were washed 5 times with ddH$_2$O. Assay Conditions: Dextransucrase in 1% (v/v) Triton X-100, 0.4 units per well (where 1 unit is the number of nmoles of glucose incorporated per minute), was incubated on the primed plates for 30 minutes at room temperature. After washing with ddH$_2$O, 100 μL of sucrose standards (diluted in 50 mM sodium phosphate, pH 6.0, 0.5% Triton X-100) were added and reactions were incubated for 60 minutes at 37° C. Plates were washed again with ddH$_2$O. One hundred microliters per well of anti-dextran antibody from ascites fluid was then added (diluted 10,000 fold in PBS containing 0.05% Tween 20) and plates were incubated for 30 minutes at 37° C. Plates were washed again with ddH$_2$O. A 100 μL aliquot of the secondary antibody, goat anti-mouse peroxidase conjugate (BRL Scientific) at 1 μg.mL$^{-1}$ was added to detect bound primary antibody. Plates were incubated for 30 minutes at 37° C. and then washed with ddH$_2$O. One hundred microliters per well of peroxidase substrate (2 mg.mL$^{-1}$ o-phenylenediamine in 0.1 M sodium acetate, pH 6.0, 0.1% hydrogen peroxide) was added to each well and the plates were incubated at room temperature for 30 minutes. Color development was stopped with the addition of 25 μL per well of 20% (v/v) sulfuric acid. Absorbance was read on a Spectramax 340 plate reader. The results are shown in FIG. 1. The NUNC Covalink plates with non-covalent attachment and the Corning Costar amine plates with covalent attachment show strong absorbance responses above a sucrose level of about 1 μg.mL$^{-1}$.

EXAMPLE 6
Comparison of Assay Absorbances with Varying Dextran Molecular Weights The assay method was carried out three times, once using no primer, once using dextran with a molecular weight of 11.5 kDa, and once using dextran with a molecular weight of 41 kDa. The dextran was attached covalently to NUNC Covalink plates (available from VWR Canlab, Toronto, Ontario). A 2.5% stock solution of each of the two dextrans was prepared in PBS and then serially diluted with PBS. Sodium cyanoborohydride (3.75%) was added to the dextran solution, 100 μL per well was added to plates, and the plates were incubated overnight at 52° C. After derivatization, plates, covalent and non-covalent, were washed 5 times with ddH$_2$O. Assay Conditions: Dextransucrase in 1% (v/v) Triton X-100, 0.4 units per well (where 1 unit is the number of nmoles of glucose incorporated per minute), was incubated on the primed plates for 30 minutes at room temperature. After washing with three 250 μL portions of ddH$_2$O, 100 μL of sucrose standards (diluted in 50 mM sodium phosphate, pH 6.0, 0.5% Triton X-100) were added and reactions were incubated for 60 minutes at 37° C. Plates were washed again with ddH$_2$O. One hundred microliters per well of anti-dextran antibody from ascites fluid was then added (diluted 10,000 fold in PBS containing 0.05% Tween 20) and plates were incubated for 30 minutes at 37° C. Plates were washed again with ddH$_2$O. A 100 μL aliquot of the secondary antibody, goat anti-mouse peroxidase conjugate (BRL Scientific) at 1 μg.mL$^{-1}$ was added to detect bound primary antibody. Plates were incubated for 30 minutes at 37° C. and then washed with ddH$_2$O. One hundred microliters per well of peroxidase substrate (2 mg.mL$^{-1}$ o-phenylenediamine in 0.1 M sodium acetate, pH 6.0, 0.1% hydrogen peroxide) was added to each well and the plates were incubated at room temperature for 30 minutes. Color development was stopped with the addition of 25 μL per well of 20% (v/v) sulfuric acid. Absorbance readings were obtained on a Spectramax 340 plate reader at 490 and 630 nm for 0.5 mg/mL sucrose and a blank containing no sucrose. The differences in absorbance readings (490 nm–630 nm) between the sucrose and blank solutions are presented in Table 1.

TABLE 1

| Absorbance Readings for Different Primers | | | |
|---|---|---|---|
| Concentration | 11.5 kDa | 41 kDa | No Primer |
| 2.5% | 0.517 | 1.262 | — |
| 0.5% | 0.424 | 1.065 | — |
| 0.1% | 0.499 | 1.276 | — |
| 0.02% | 0.262 | 1.154 | — |
| 0.004% | 0.009 | 0.938 | — |
| 0 | not determined | not determined | 0.069 |

EXAMPLE 7
Comparison of Results with Different Dextransucrase Reaction Times

Figure 2:
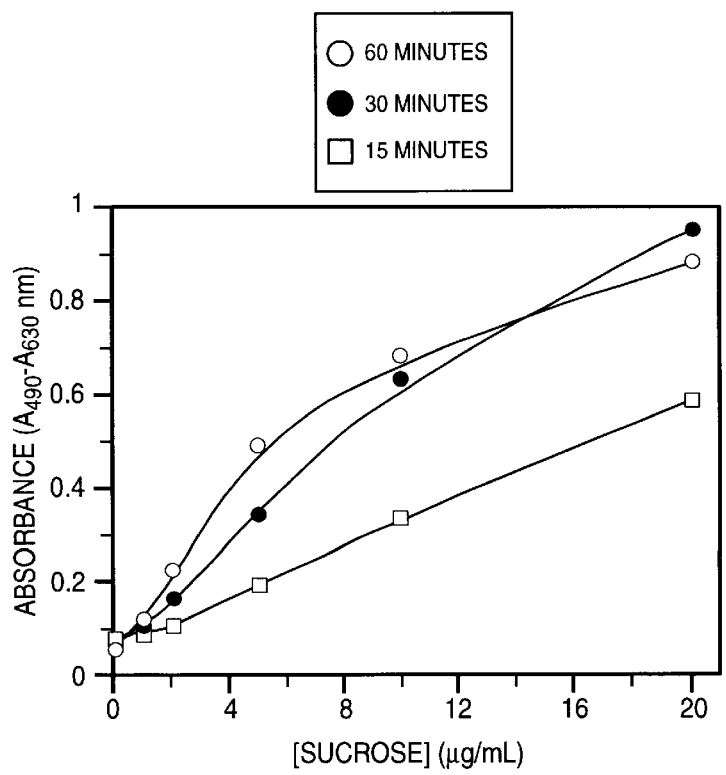
FIG. 2 is a graph showing the measured absorbance as a function of sucrose concentration for three different dextransucrase reaction times.

Immulon 2 plates were derivatized with 100 μL per well of a 0.25% dextran solution in 5% Triton X-100. The assays were performed as described in Example 6, except that the dextransucrase reaction time in the three experiments was 15 minutes, 30 minutes, and 60 minutes. The results are shown in FIG. 2. The 15 minute incubation period produced the best linear response, with a sensitivity to sucrose concentration as low as 1 μg.mL$^{-1}$.

EXAMPLE 8
Effect of Glucose

Figure 3:
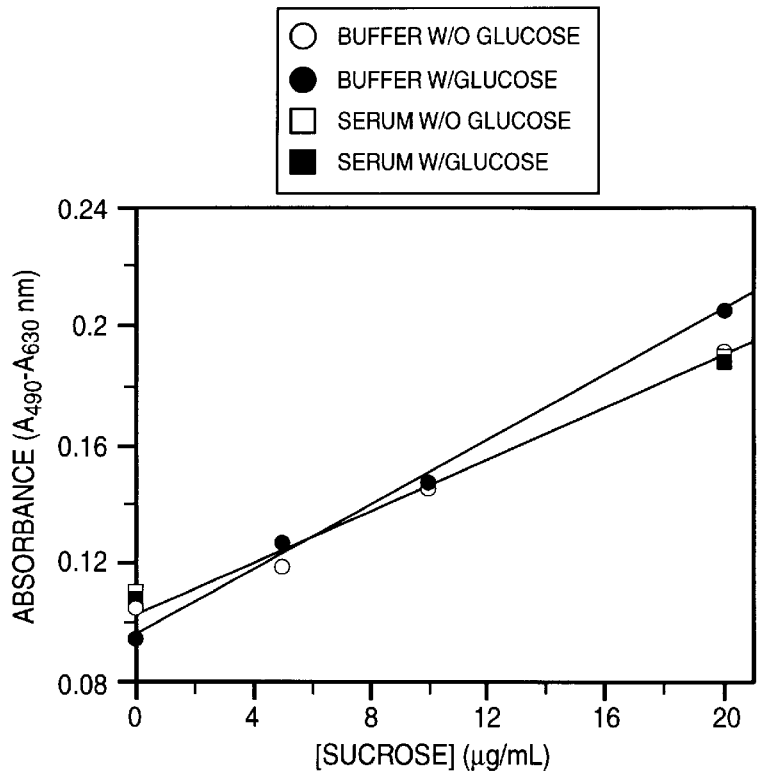
FIG. 3 is a graph showing the measured absorbance as a function of sucrose concentration in samples of serum and buffer, with and without glucose.

The samples were prepared by mixing 900 μL of sucrose stock standards (diluted in 50 mM sodium phosphate, pH 6.0, 0.5% Triton X-100) with 100 μL of glucose from an 80 mM stock in buffer, or with 100 μL of buffer alone. Two sucrose standards, 0 and 20 μg.mL$^{-1}$, were prepared by mixing 700 μL of 0 or 29 μg.mL$^{-1}$ of sucrose stock standards with 100 μL of glucose or 100 μL of buffer and 200 μL of serum (Fisher Scientific). Assays were performed as described in Example 6. FIG. 3 shows the standard curve for the determination of sucrose and the effects of serum and glucose; buffer without glucose (open circles), buffer with 8 mM glucose (closed circles), serum without glucose (open squares) and serum with 8 mM glucose (closed squares).

EXAMPLE 9

Preparation of Conjugated Anti-Dextran Antibody

A five-milliliter aliquot of ascites fluid containing monoclonal antibody to dextran was centrifuged to remove particulate matter. Clarified supernatant was loaded into an Ultrafree-15 Centrifugal Filter Device containing a BioMax-100k NMWL membrane (Millipore, Bedford, Mass.) and the antibody solution was concentrated by centrifugation according to the manufacturer's instructions. Protein concentration was determined by reading absorbance at 280 nm according to the procedure of Sambrook et al., Molecular Cloning—A Laboratory Manual, Cold Spring Harbor Laboratory Press (1989). Antibody protein was coupled to horseradish peroxidase. Primary amines of the antibody were reacted with N-succinimidylc-S-lacetylthioacetate followed by deacetylation to generate free sulfhydryl groups, which were subsequently reacted with maleimide-activated horseradish peroxidase, using EZ-Link™ Maleimide Activated Horseradish Peroxidase Kit (Pierce, Rockford, Ill.) according to the manufacturer's instructions.

Figure 4:
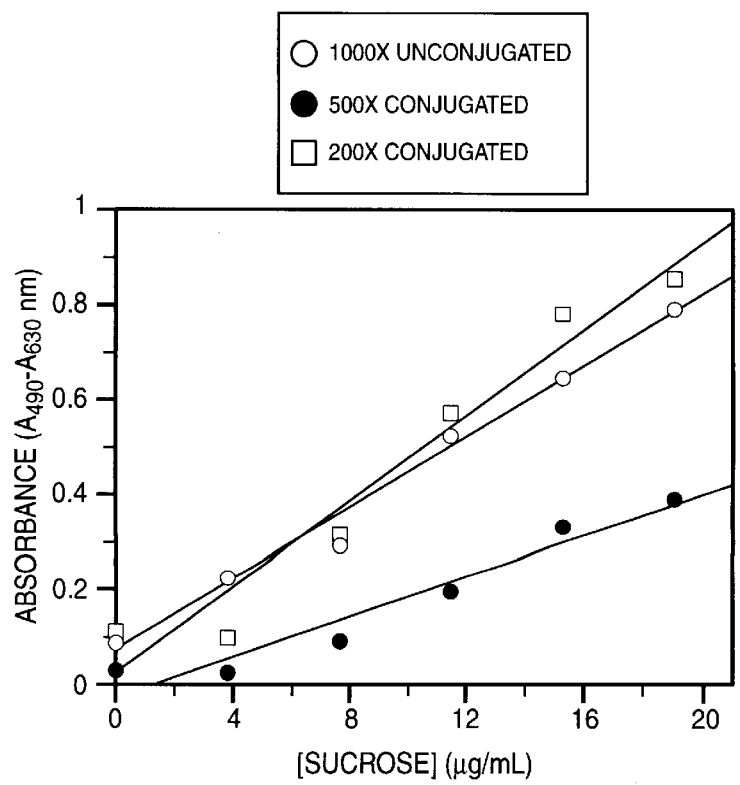
FIG. 4 is a graph showing the absorbance response as a function of sucrose concentration for conjugated and unconjugated primary antibody.

Sucrose detection was carried out as described in Example 4, except that the conjugated anti-dextran antibody was used in place of the mouse anti-dextran antibody, rendering subsequent addition of the secondary antibody unnecessary. Two different dilutions of conjugated antibody were used and the results compared to those from one dilution of the unconjugated antibody in a dual antibody system. The results are shown in FIG. 4. The 200× dilution of the conjugated antibody displays an absorbance response similar to that of the 1000× dilution of the unconjugated antibody. Hence, the same signal can be achieved for a given sucrose concentration using either the conjugated or unconjugated antibody.

Other variations and modifications of this invention will be obvious to those skilled in the art. This invention is not limited except as set forth in the claims.

What is claimed is:

1. A method for assaying sucrose in a biological fluid, said method comprising the steps of:
   (a) coating a substrate with (i) a glucose or fructose polymer selected from the group consisting of amylose, dextran and levan and (ii) a sucrose transgylcosidase enzyme corresponding to said selected glucose or fructose polymer:
   (b) incubating the coated substrate with a biological fluid; and
   (c) determining an amount of sucrose present in the fluid by measuring an increase in an amount of the glucose or fructose polymer; wherein step (c) comprises the steps of:
      (i) incubating said substrate with a carbohydrate-binding protein, said protein being an anti-dextran antibody if the substate is coated with dextran, an amylose-binding protein if the substrate is coated with amylose, or an anti-levan antibody if the substrate is coated with levan;
      (ii) incubating said substrate with a secondary antibody; and
      (iii) adding to said substrate a solution containing a detecting agent, and determining the amount of sucrose in the fluid by measuring light absorption of the solution.

2. The method of claim 1, wherein the secondary antibody is a conjugate comprising (i) an antibody which will bind to the anti-dextran antibody, amylose-binding protein or anti-levan antibody and (ii) a marker enzyme.

3. A method for assaying sucrose in a biological fluid, said method comprising the steps of:
   (a) coating a substrate with (i) a glucose or fructose polymer selected from the group consisting of amylose, dextran and levan and (ii) a sucrose transgylcosidase enzyme corresponding to said selected glucose or fructose polymer;
   (b) incubating the coated substrate with a biological fluid; and
   (c) determining an amount of sucrose present in the fluid by measuring an increase in an amount of the glucose or fructose polymer; wherein step (c) comprises the steps of:
      (i) incubating said substrate with a conjugate comprising (1) a carbohydrate-binding protein, said protein being an anti-dextran antibody if the substate is coated with dextran, an amylose-binding protein if the substrate is coated with amylose, or an anti-levan antibody if the substrate is coated with levan; and (2) a marker enzyme; and
      (ii) adding to said substrate a solution containing a detecting agent, and determining the amount of sucrose in the fluid by measuring light absorption of the solution.

4. The method of claims 2 or 3, wherein the marker enzyme is a peroxidase enzyme.

5. The method of claim 4, wherein the peroxidase enzyme is horseradish peroxidase.

6. The method of claim 5, wherein the detecting agent comprises hydrogen peroxide and a compound which oxidizes to form a chromophore which strongly absorbs visible light in amounts effective to produce a solution having a detectable absorption of visible light.

7. The method of claim 6, wherein the glucose or fructose polymer is dextran.

8. The method of claim 7, wherein the sucrose transglycosidase enzyme is dextransucrase.

9. The method of claim 8, wherein the carbohydrate-binding protein is mouse anti-dextran antibody.

10. The method of claim 9, wherein the detecting agent comprises hydrogen peroxide and o-phenylenediamine.

11. The method of claim 10, wherein the sucrose level is determined from a measurement of light absorption at 490 nm.

12. The method of claim 11, wherein the sucrose level is determined from a difference between a measurement of light absorption at about 490 nm and a measurement of light absorption at about 630 nm.

13. The method of claim 2, wherein the conjugate comprises goat anti-mouse IgG and horseradish peroxidase.

* * * * *

UNITED STATES PATENT AND TRADEMARK OFFICE
CERTIFICATE OF CORRECTION

PATENT NO. : 5,972,631

DATED : October 26, 1999

INVENTORS : THOR JON BORGFORD ET AL.

It is certified that error appears in the above-identified patent and that said Letters Patent is hereby corrected as shown below:

COLUMN 1:
Line 44, "including;" should read --including:--.
Line 60, "and or" should read --and/or--.

COLUMN 6:
Line 29, "Immnulon 2" should read --Immulon 2--.

COLUMN 9:
Line 57, "500" should read --50%--.

COLUMN 10:
Line 60, "0.50%." should read 0.5%--.

COLUMN 11:
Line 7, "ddH$_2$0" should reed --ddH$_2$O--.
Line 8, "1 AL.mL$^{-1}$" should read --1 $\mu$L.mL$^{-1}$--.

COLUMN 12:
Line 18, "ascities" should read --ascites--.

COLUMN 13:
Line 22, "N-succinimidylc-S-lacetylthioacetate" should read
    --N-succinimidyl-S-acetylthioacetate--.
Line 25, "Rockf ord, Ill.)" should read --Rockford, Ill.)--.
Line 55, "wherein" should read --¶ wherein--.
Line 59, "substate" should read --substrate--.

UNITED STATES PATENT AND TRADEMARK OFFICE
CERTIFICATE OF CORRECTION

PATENT NO. : 5,972,631

DATED : October 26, 1999

INVENTORS : THOR JON BORGFORD ET AL.

It is certified that error appears in the above-identified patent and that said Letters Patent is hereby corrected as shown below:

<u>COLUMN 14</u>:
Line 23, "wherein" should read --¶ wherein--.
Line 27, "substate" should read --substrate--.

Signed and Sealed this

Seventh Day of November, 2000

Attest:

Q. TODD DICKINSON

*Attesting Officer*      *Director of Patents and Trademarks*